(12) United States Patent
Brummel et al.

(10) Patent No.: US 7,703,042 B2
(45) Date of Patent: Apr. 20, 2010

(54) SYSTEM AND METHOD FOR A SEAMLESS USER INTERFACE FOR AN INTEGRATED ELECTRONIC HEALTH CARE INFORMATION SYSTEM

(75) Inventors: Tony Brummel, Middleton, WI (US); Carl D. Dvorak, Madison, WI (US); Khiang Seow, Madison, WI (US); Daniel Bormann, Waunakee, WI (US); Steve Larsen, Madison, WI (US); Andrew Ma, Madison, WI (US); Aaron T. Cornelius, Mount Horeb, WI (US)

(73) Assignee: Epic Systems Corporation, Madison, WI (US)

( * ) Notice: Subject to any disclaimer, the term of this patent is extended or adjusted under 35 U.S.C. 154(b) by 0 days.

(21) Appl. No.: 11/839,251

(22) Filed: Aug. 15, 2007

(65) Prior Publication Data
US 2008/0033761 A1 Feb. 7, 2008

Related U.S. Application Data

(63) Continuation of application No. 10/007,620, filed on Dec. 5, 2001, now Pat. No. 7,275,220.

(60) Provisional application No. 60/257,970, filed on Dec. 22, 2000.

(51) Int. Cl.
*G06F 3/00* (2006.01)

(52) U.S. Cl. .................. 715/804; 715/781; 715/700; 705/2; 705/3; 706/45; 707/1

(58) Field of Classification Search ................ 715/700, 715/741, 743, 762, 764, 765, 781, 792, 804, 715/810, 835, 866; 705/1, 2, 3; 706/45, 706/46, 47; 707/1, 3, 9, 100, 104.1; 600/300
See application file for complete search history.

(56) References Cited

U.S. PATENT DOCUMENTS

| | | | | |
|---|---|---|---|---|
| 6,004,276 A * | 12/1999 | Wright et al. | ............... | 600/508 |
| 6,401,138 B1 * | 6/2002 | Judge et al. | ................. | 719/328 |
| 6,912,549 B2 * | 6/2005 | Rotter et al. | ................ | 707/200 |
| 6,971,067 B1 * | 11/2005 | Karson et al. | ............... | 715/777 |
| 7,424,679 B1 * | 9/2008 | Lamer et al. | ................ | 715/737 |
| 2002/0022973 A1 * | 2/2002 | Sun et al. | ........................ | 705/3 |
| 2002/0023067 A1 * | 2/2002 | Garland et al. | ................. | 707/1 |
| 2002/0054053 A1 * | 5/2002 | Naimi et al. | ................ | 345/700 |
| 2002/0107875 A1 * | 8/2002 | Seliger et al. | ............... | 707/200 |

* cited by examiner

*Primary Examiner*—X. L Bautista
(74) *Attorney, Agent, or Firm*—Boyle Frederickson, S.C.

(57) ABSTRACT

An interface for a medical record database allows multiple different applications to be opened accessing the records of a common and/or different patients. For those applications accessing the records of a common patient, a visual indication is provided indicating whether or not records of the same patient are being accessed to prevent the user from mistakenly comparing the records of different patients.

8 Claims, 9 Drawing Sheets

SYSTEM AND METHOD FOR A SEAMLESS USER INTERFACE FOR AN INTEGRATED ELECTRONIC HEALTH CARE INFORMATION SYSTEM

CROSS REFERENCE TO RELATED APPLICATION

This application is a continuation on U.S. application Ser. No. 10/007,620 filed Jan. 5, 2001 now U.S. Pat. No. 7,275,220 which is a continuation-in-part of, and claims priority to, U.S. Provisional Patent Application Ser. No. 60/257,970, entitled: "Seamless User Interface Built on a Single Data Repository for an Integrated Electronic Health Care Information System," filed Dec. 22, 2000 the disclosure of which is hereby expressly incorporated herein by reference.

STATEMENT REGARDING FEDERALLY SPONSORED RESEARCH OR DEVELOPMENT

--

BACKGROUND OF THE INVENTION

The present invention relates generally to health records management, and more particularly, to a seamless user interface adaptable to an integrated electronic health care system.

Electronic medical record and practice management information systems store, retrieve and deliver information to a health care enterprise. Some systems address only one type of information necessary for clinical and practice management, for example, outpatient billing information records, outpatient medical records information, etc. Such systems feature single user interfaces, each allowing entry of only one limited type of information, and are combined with a single data repository that is similarly limited. The data repositories utilized by these systems can be difficult to interface with one another, and typically include duplicate information.

Other systems allow multiple user interfaces to access a single data repository, however the multiple user interfaces are disparate in operation and appearance. Facilities implementing such disparate interfaces must expend significant time and effort to train users for each of the confusing variety of applications with unrelated user interfaces. In addition, such systems typically limit users' ability to move freely within one application requiring, for example, that users complete a specified task before moving on to another. Further, such systems typically require that two individual programs run simultaneously on one machine when switching between applications.

The systems mentioned require complicated deployment of multiple user interfaces and/or data repositories to different system users and access terminals throughout the health care facility. Health care enterprises utilizing such systems risk non-compliance with health care regulations and best practice guidelines, due to the inflexibility of the multiple interfaced applications with different system user security records and alerts systems. Additionally, the health care enterprises incur unnecessary administrative overhead created by the poor communication capabilities between the multiple interfaced applications, for example, poor or non-existent clinical decision support, or billing applications that contradict diagnostic decisions already filed in the enterprise's medical records application.

DETAILED DESCRIPTION OF THE PREFERRED EMBODIMENT

Figure 1:
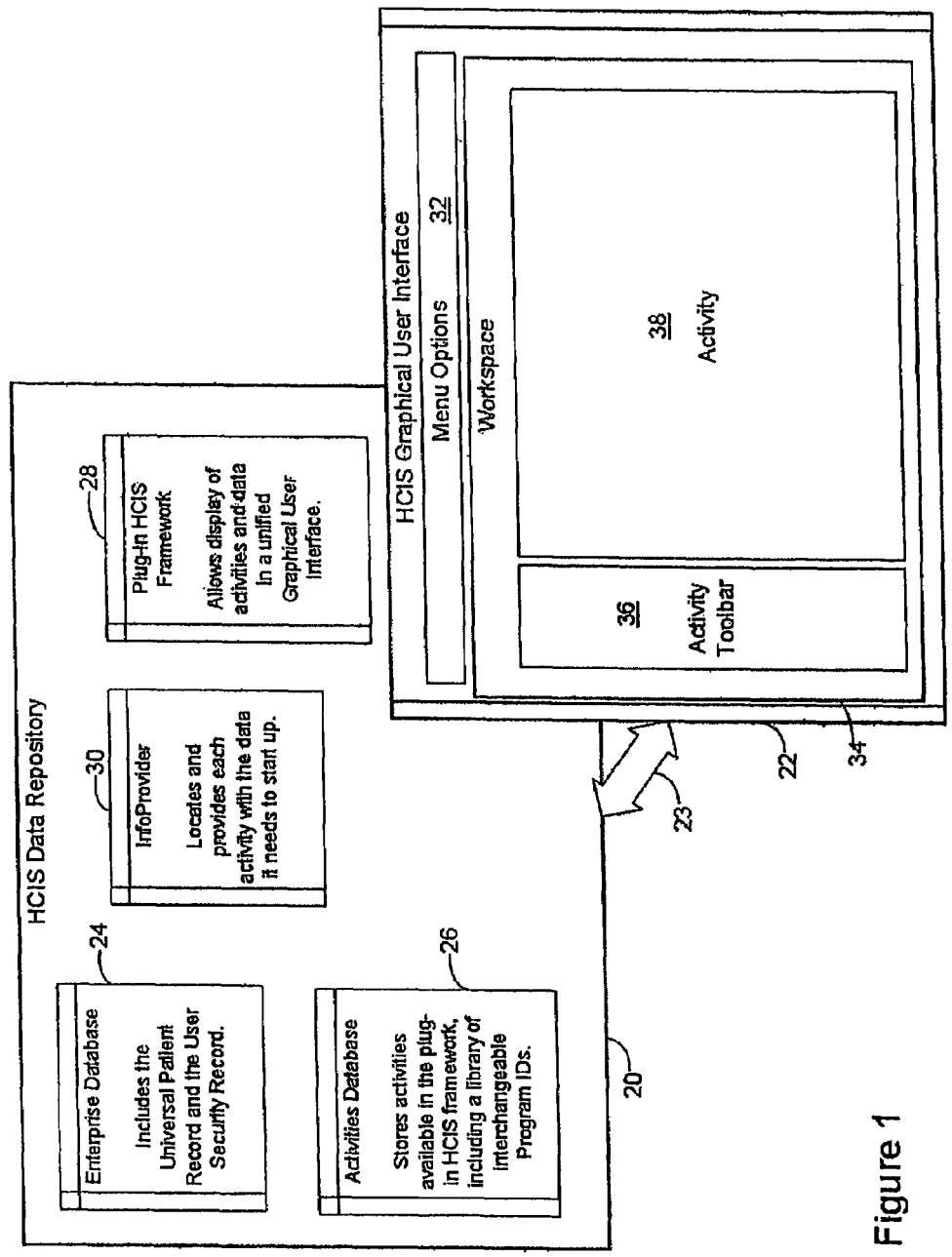
FIG. 1 is a graphical representation illustrating interaction between a health care information system database repository and a health care information system graphical user interface according to a preferred embodiment of the invention.

An electronic Health Care Information System (HCIS) is provided including a modular framework and a display in communication with the modular framework for providing a graphical user interface to a system user. The modular framework includes a plurality of activities, where each activity provides an aspect of patient care. Activities for providing aspects of patient care include, but are not limited to, activities used in the providing of health care to a patient (for example, which provide a care provider with patient medical information such as a patient history activity and a chart review activity, etc.) and activities used in the management of health care for a patient (for example, registration, patient demographics, etc. activities). The graphical user interface is adaptable for displaying information corresponding to one or more of the activities, and includes a common menu format for communicating available operations in the graphical user interface, and common visual components for displaying information to a system user.

The modular framework allows additional activities to be added to the system without the difficulties associated with interfacing and configuring the activities to work with the HCIS and with each other. Further, the ease of integrating applications due to the modular framework results in a high rate of compliance with government regulations. The common menu structures and common visual components provided by the graphical user interface provide system users with a consistent interface for the HCIS, reducing the training requirements of system users who might otherwise be cross trained on multiple user interfaces. Additionally, the graphical user interface and modular framework allows system users to freely switch between activities available within the HCIS, even before completing a particular activity. The system users are therefore not forced into finishing a particular activity before gaining access to another activity, allowing for example, emergency situations to be addressed immediately without loss of information or work flow in an interrupted activity. Further, the graphical user interface and modular framework facilitates the combining of heterogenous, but related, activities within particular workflow (for example, work space).

In further embodiments, a single information database is provided for use by the activities, reducing if not eliminating data duplication between activities, and the difficulties with interfacing multiple databases having varying structure or format. Additionally, the single information database allows a common security record to be kept for system users, facilitating uniformity of security access for system users across all activities of the HCIS, ease of setting security requirements for new system users, and reduced probability of granting mistaken security privileges as security information for all activities need be entered but once. Further, the single information database and modular framework allows an alert system to be provided to warn system users where information entered in an activity conflicts with other information for a particular patient in the information database. Additionally, system users are provided the ability to configure the graphical user interface, giving the flexibility of tailoring the graphical user interface to offer functionality and information to better serve their specific needs. In addition, a workflow management tool is provided as an Electronic Messaging and Workflow System, further discussed below.

Referring to FIG. 1, a single information database (a Health Care Information System ("HCIS") data repository 20) is in communication with an HCIS graphical user interface 22 using a communications link 23, where the data repository supports a modular ("plug-in") activity structure, in accordance with a preferred embodiment of the invention. The HCIS data repository 20 includes an enterprise database 24 which stores information related to system users and patients, including a universal patient record having data collected for each patient, and user security records defining security parameters for system users, maintaining a single data record per system user and patient. Further information regarding the universal patient record may be found in U.S. patent application "System And Method For Integration Of Health Care Records," to Dvorak et al., Ser. No. 10/007,066, filed Dec. 5, 2001, and hereby incorporated by reference herein. The HCIS data repository 20 further includes an activities database 26 which stores the activities available in the plug-in HCIS framework. The activities database 26 includes a library of interchangeable program identifications and data requirements for each activity which are used in building the graphical user interface 22, further discussed below. The HCIS data repository 20 further includes a modular (plug-in) framework 28 and an information provider 30, in communication with each other, and with the enterprise database 24 and the activities database 26. The plug-in framework 28, utilizing information from the activities database 26, is capable of composing and presenting each available activity to a system user in a unified graphical interface, as discussed below. Because the activities database 26 includes interchangeable program identifications, the HCIS graphical user interface 22 provides a unified look and common convention including a common menu format and common visual components. The information provider 30 locates and provides each activity to be initiated with the data it needs to start up, allowing each activity to be launched at any time without the necessity of obtaining data in each different context. Thus, when an activity is launched, the HCIS framework functionality 28 requests the information provider 30 to provide necessary data for launching the activity based on the data requirements provided by the activities database 26. For example, where the activity is patient-specific, therefore requiring a patient identification in order to open, the information provider 30 determines how to provide the patient identification in the current context (system user environment), further discussed below.

In a preferred embodiment, the single data repository 20 is a server, where the enterprise database 24 and the activities database 26 are embodied in a storage device, for example a hard drive, within the server. The functionality provided by the information provider 30 and the plug in framework 28 are programs running on a suitable processor within the server. The program identifications are program modules for forming specific functions which may be combined to form the functionality for a particular activity. The plug-in framework receives these program modules, or program address links for accessing the program modules, along with the data corresponding to the data requirements for the particular activity, and is able to provide the particular activity to the system user via the graphical user interface.

The HCIS graphical user interface 22 communicates with the data repository 20 via the communications link 23, allowing system users to access various activities provided by the HCIS system. The communication link 23 may represent the internet, a dedicated data bus, or any other means for communicating information between the HCIS data repository 20 and the HCIS graphical user interface 22, as would be appreciated by one skilled in the art. The HCIS graphical user interface 22 includes a menu 32 in a common menu format across activities and operations (workspaces), providing the system user with options for opening various workspaces, for example the workspace 34. The workspace 34 may allow handling of operations in a particular system user environment, for example handling patient admission and other patient encounters, scheduling, etc. as discussed below. The workspace 34 includes an activity toolbar 36 listing activities available to the system user within the particular workspace, where a particular activity selected by the system user is displayed in an activity display area 38. Activities may be nested within the work space 34 and are typically dynamically built according to information the InfoProvider 30 delivers from the universal patient record and user security record of the enterprise database 24 and the activities database 26. Users may select tabs on the activity toolbar 36 to move freely between any combination of available activities without closing the workspace 38 or reentering information that is already available within the workspace context. Certain data combinations in the patient record may trigger alerts and requests for further data entry. These requests may automatically open new activities for the user, compelling compliance with enterprise-defined guidelines. Further, access to viewing and editing information may also be limited in accordance with the system user's single user security record. Operation of and interaction between the HCIS data repository 20 and HCIS graphical user interface 22 are described with respect to FIGS. 2 and 3, in accordance with embodiments of the invention.

Figure 2:
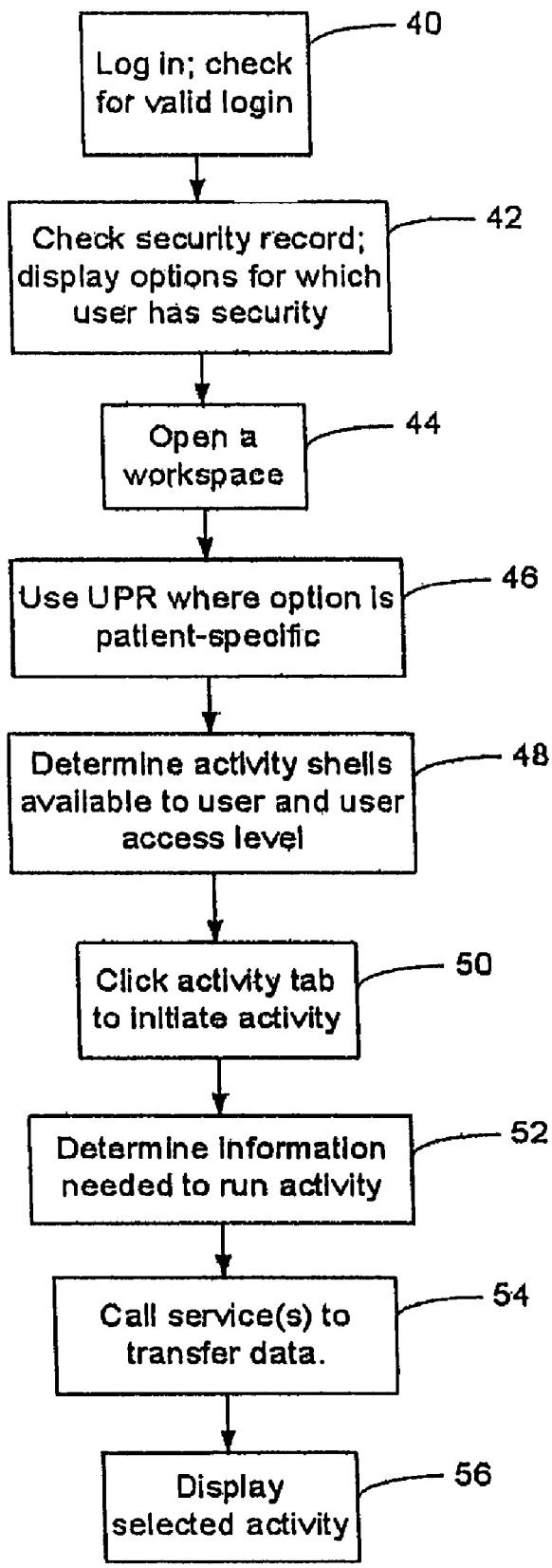
FIG. 2 is a flowchart illustrating interaction between the data repository and the graphical user interface configuration of FIG. 1 in accordance with an embodiment of the invention.

Referring to FIG. 2, a user logs into the HCIS system using, for example a user terminal (not shown) displaying the HCIS graphical user interface 22, as shown in step 40. The HCIS system prompts the user for a valid log-in identification before access to the HCIS system is allowed. Upon a successful log-in to the HCIS system, the enterprise database 24 is searched for a user security record corresponding to the user identification, where the user security record defines all security parameters for that particular system user, step 42. Only menu options (for example, workspaces) for which the system user has appropriate security clearance, as determined from the enterprise database 24, appear on the menu 32. The system user may select a menu option from the menu 32, which opens a corresponding workspace 34 as shown in step 44. Where specific data is required to open the workspace, for example patient information, the information provider 30 retrieves the information from a universal patient record of the enterprise database 24, step 46. The HCIS system further checks the system user's security record of the enterprise database 24 to determine which activities within the workspace 34 the system user has sufficient security clearance to access step 48. Those activities for which the system user has security clearance to access appear within the activity toolbar 36 as activity tabs (not shown), and the user may select a specific activity tab within the activities toolbar to initiate the activity, step 50. The user may select the particular activity tab using, for example, a mouse device (not shown) connected to the user terminal where the activity is selected by a click of a mouse button. Alternatively, the activity may be selected utilizing a predetermined key of a keyboard (not shown) connected to the user terminal, or where the HCIS graphical user interface includes a touch responsive screen, the desired activity may be selected utilizing, for example, a stylus (not shown).

Upon selection of an activity, the activities database 26 is queried to determine which information is needed to run that particular activity, for example which program identifications and data requirements, step 52. In step 54, the information provider 30 is requested to call the appropriate services for transferring the data needed for the particular activity to start up. For example, the information provider 30 may call services which search the enterprise database 24 for the necessary data. Where the data is not present in the enterprise database 24, the information provider 30 may call services to prompt the system user for the information. Additionally, the information provider 30 may determine data using other activities open within the workspace. For example, where a new activity requires a patient identification to open, the information provider 30 may determine the patient identification from other activities open within the workspace. The information provider may then attain additional data by transferring the data from the open activity to the new activity, or for example, by searching the enterprise database 24 using the patient identification to determine the necessary data.

The necessary data is provided to the plug-in framework 28, which utilizes the program identifications from the activities database 26 and the data from the information provider 30 to open the new activity in the activity display area 38, step 56. The activities database includes interchangeable program identifications for the activities, allowing the plug-in framework to maintain a common menu format and common visual components when causing information to be displayed on the graphical user interface 22. The graphical user interface 22, because of the common menu formats and common visual components, allows system users to intuitively switch between workspaces and activities without additional and time-consuming training for each activity, unlike the disparate menu formats and visual components utilized by the multiple interfaced systems of the prior art.

Additionally, the plug-in framework 28 and single data repository 20 allow additional activities and workspaces to be easily integrated with the HCIS. The new activities and/or workspaces with corresponding required program identifications are added to the activities database 26 along with the data requirements for the new activities. Utilizing such a modular structure facilitates adding activities to the system without the difficulty of interfacing several separate user interfaces, and further, having a single data repository overcomes the difficulties of interfacing various separate databases. Further, as discussed above, utilizing the activities database 26 with interchangeable program identifications allows a common menu format and common visual components to be used in various workspaces and activities, reducing a health enterprise's overhead associated with training users on a health care information system.

In another embodiment, the system user may open multiple workspaces at one time, and switch between the workspaces as desired utilizing, for example, the mouse, a predetermined key, or a stylus (where a touch sensitive screen is provided) as discussed above. Further, multiple activities within a single workspace may be opened, where the user may similarly switch between the opened activities at any time. Thus, the system user is allowed to freely switch between available activities and workspaces at any moment, whether or not a particular activity is complete. This provides the system user with flexibility to immediately handle various situations and circumstances which may arise, for example emergency situations, without having to complete a current activity, and without loss of information or work progress within an interrupted activity.

Figure 3:
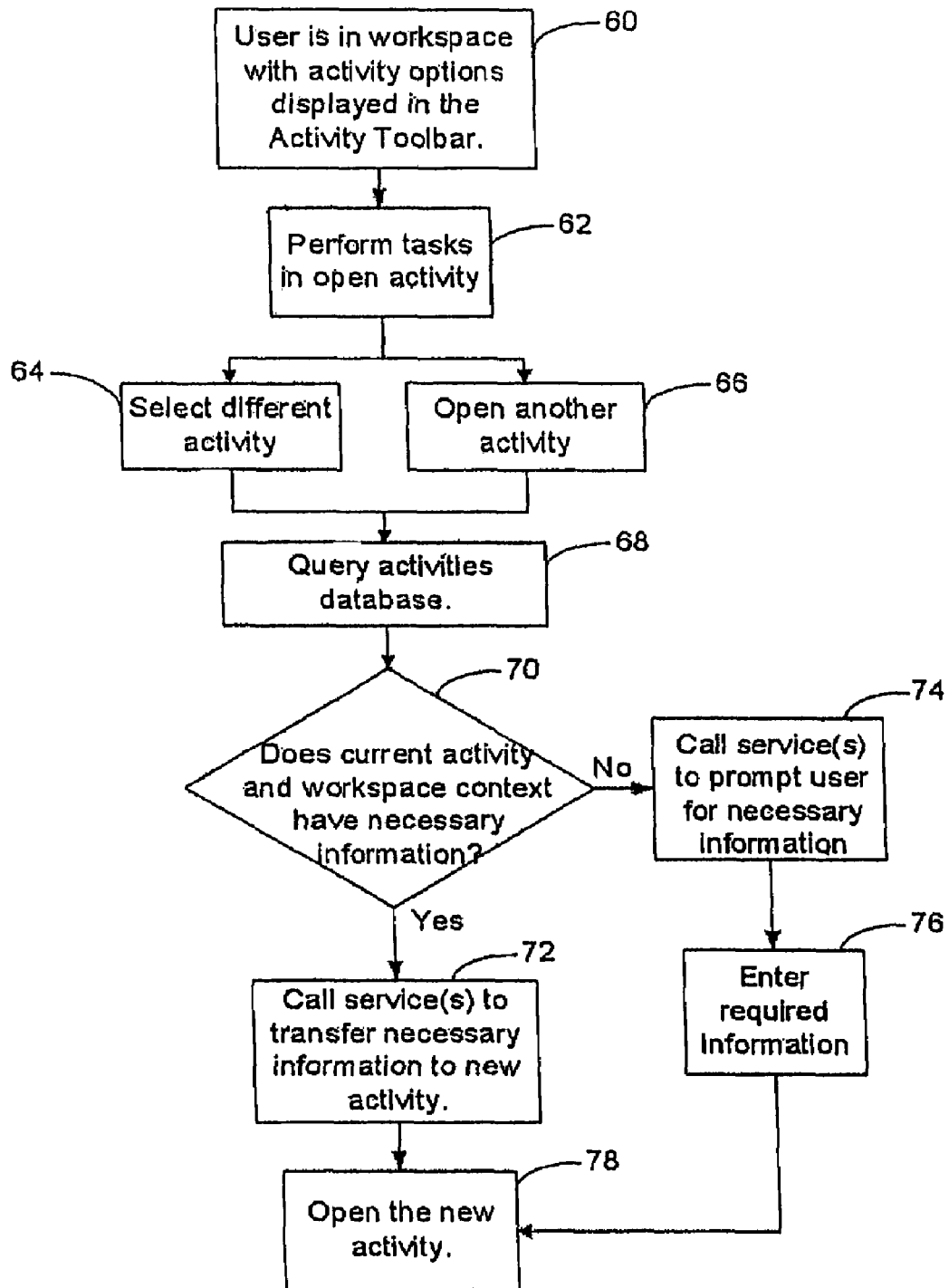
FIG. 3 is a flow chart illustrating the steps for allowing a user to switch between activities within a workspace in accordance with an embodiment of the invention.

In another embodiment, in addition to a user selecting activities to be displayed within the workspace, the HCIS system may cause an activity to open responsive to information entered by the system user. For example, information entered by the system user indicating an emergency disposition in a patient call documentation activity of a patient call workspace may automatically cause an activity for scheduling an emergency room visit to open on the graphical user interface. Additionally, information entered by the system user in combination with data already present in the specific patient's record may trigger an alert in the HCIS system, automatically opening another activity on the graphical user interface 22. FIG. 3 is a flow chart illustrating a switch from one activity to another within a workspace in accordance with an embodiment of the invention.

Where the system user is in a workspace with a number of activity options displayed in the activity toolbar 36, step 60, the system user performs a task within the activity that is currently open in the activity display area 38, step 62. This may occur, as shown in FIG. 3, by the user selecting a different activity in the workspace 34, step 64, or where the system opens another activity due to information entered by the system user, step 66. Upon selection or opening of another activity, the activities database 26 is queried to determine what program identifications and necessary data, for example a patient identification, are necessary to open the new activity, step 68. The information provider 30 examines a current activity(ies) in the activity display area 38 and the workspace context for the necessary data, for example a patient identification from an open activity in the workspace, step 70. Where it is determined that a patient identification is present in an open activity in the workspace, the information provider 30 calls services that transfer the necessary information (here, the specific patient information) to the new activity, as shown in step 72, and the new activity is opened, step 78. However, where the necessary data is not available in the current activity context, the information provider calls a service that prompts the user for the necessary information, for example entry of a patient identification, step 74. This information may be prompted using a dialog window displayed on the graphical user interface 22, for example within the activities display area 38, as would be appreciated by one skilled in the art.

In step 76, the system user enters the required information, and the system opens the new activity, step 78. The information provider 30 is capable of obtaining the information that a particular activity needs to open in any context by calling the particular service that provides the information to the activity from a variety of sources, for example workspace context, database, user entry, etc., allowing the user to move with total flexibility from one activity to another, and from one workspace to another. Where an activity is selected in any context, the information provider 30 needs just be informed of the data requirements for the activity, and the information provider is wholly responsible for and adaptable to obtaining the information, at which point the activity opens.

Figure 4:
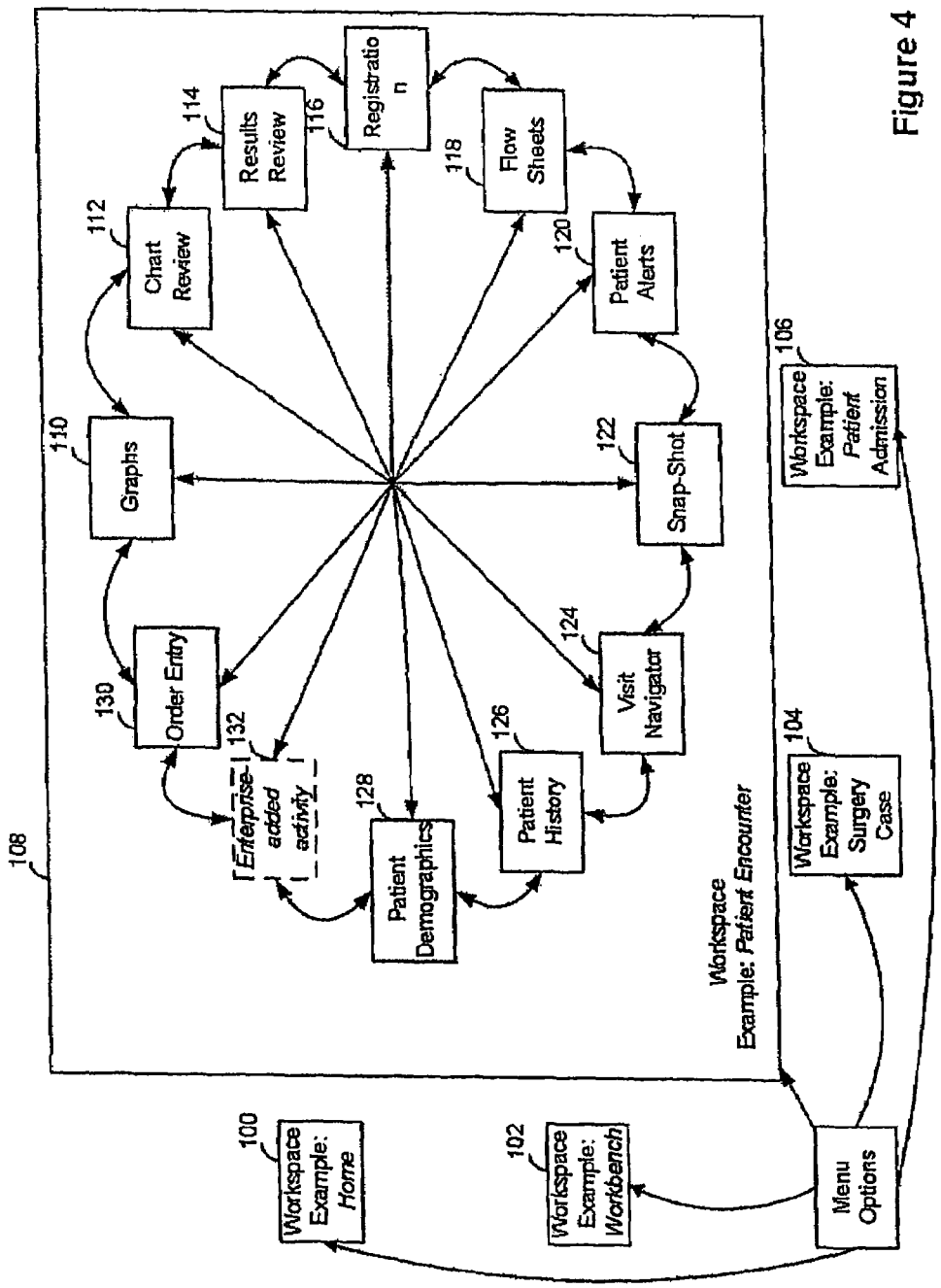
FIG. 4 is a graphic representation of multiple workspaces and multiple activities in accordance with an embodiment of the invention.

FIG. 4 illustrates an example of multiple workspaces and activities that a system user may employ simultaneously in the HCIS graphical user interface 22. For example, a home workspace 100, a workbench workspace 102, a surgery case workspace 104, a patient admission workspace 106, and a patient encounter workspace 108 may be accessible to a system user through the menu options displayed on, for example the menu 32, for a system user having sufficient security clearance. Upon opening a workspace, for example the patient encounter workspace 108, activities for which the system user has access for the particular patient appear as activity tabs (not shown) in the activity toolbar 36. For example, tabs for activities may include graphs 110, chart review 112, results review 114, registration 116, flowsheets 118, patient alerts 120, snap-shot 122, visit navigator 124, patient history 126, patient demographics 128, order entry 130, or any enterprise added activity 132 plugged into the HCIS system may appear.

Thus, from the menu options of the menu 32, the system user may open and maintain multiple workspaces simultaneously in the graphical user interface 22, where each workspace may draw on the same or a different patient record. Further, within each workspace, the system user may select any activity listed in the activities toolbar 36. The activities can be opened in any order as many times as the system user desires, providing total flexibility in accessing all activities. The workspaces and activities included and shown in FIG. 4 are exemplary in nature. Any number of workspaces, and new activities within a workspace for new purposes can be created and accessed through an open workspace. For example, other workspaces may include, but are not limited to, patient call, case, log, report, pharmacy, lab, radiology, inpatient, home, and administration workspaces. One or more of the activities 110-132 or any other activity now available including schedule, messaging, account maintenance, and patient list activities, or activities which become available in the future may be included in any workspace.

In accordance with another embodiment of the invention, the workspaces and/or activities may be user-defined. For example, the system user may define the activity tabs that appear in the activity toolbar 36. Activities may be disabled from appearing in the activity toolbar for a particular workspace, or activities from one workspace may be user-defined by the system user to appear in the activity toolbar of another workspace. Additionally, when an activity is launched, the system user may user-define what data fields are displayed within the activity display area. For example, the system user may eliminate certain data fields from appearing within a launched activity, or, may user-define specific activities to display data fields which would normally not be displayed in the activity. User-defined preferences for a system user may be stored, for example, within the HCIS data repository 20, and more specifically, may be stored in the enterprise database 24, as part of, or corresponding to, a record for the system user.

Figure 5:
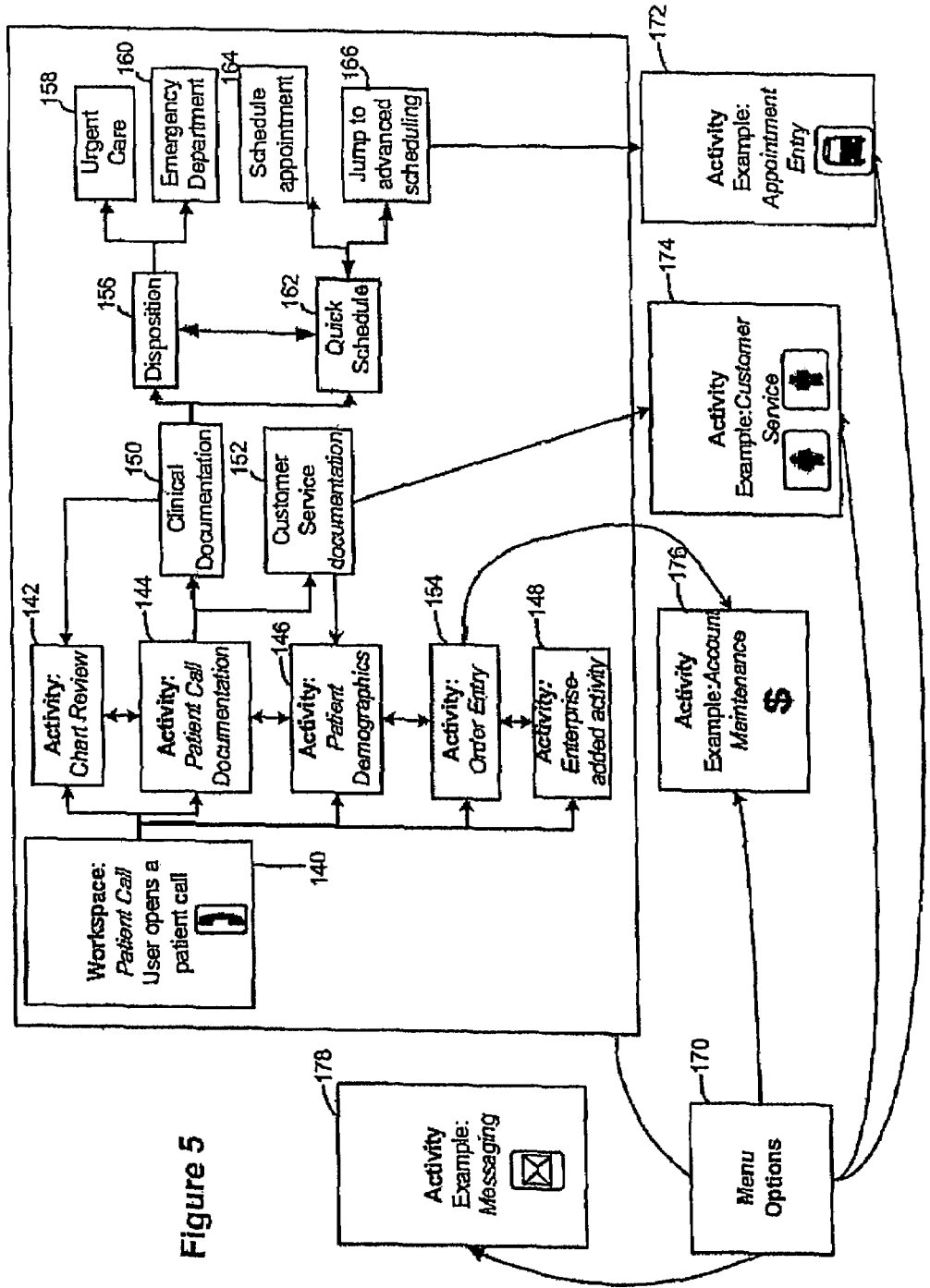
FIG. 5 is a flow chart of a sample work flow for a nurse call/nurse triage environment in accordance with an embodiment of the invention.

FIG. 5 illustrates a sample workflow for a nurse call center/nurse triage environment in accordance with an embodiment of the invention. FIG. 5 illustrates how integration via the HCIS single user interface can help health care enterprises provide more efficient, more detailed and therefore better patient care across locations. Users handling patient calls in a triage environment can access a patient's complete medical records via, for example menu options 170 of the patient call workspace 140. Multiple patient call workspaces 140, each workspace representing the same or a different patient call, may be opened on the HCIS graphical user interface, where system users are able to jump between the workspaces as desired. With any workspace, the system users may select any activity for which they have security clearance. For example, in the patient call workspace 140, the chart review activity 142, the patient call documentation activity 144, and the patient demographics activity 146, may be accessed by the system user with adequate security access. The system user may further have access to other activities, for example, appointment entry 172, customer service 174, account maintenance 176, and electronic messaging 178 activities. Such additional activities may be available through the menu options 170, or may be triggered automatically by the system, or provided to the system user in response to information entered as discussed below.

Any enterprise added activity 148 may be plugged into the HCIS graphical user interface due to the plug-in framework 28, providing additional activities (such as, for example, a call center utilizing specially customized forms such as Epic Smart Forms to collect the call information, an Intranet page for a particular organization, or other facility-specific activities). For example, upon opening a patient workspace via call center, a call center encounter is created in the patient record, which can be viewed by any authorized system user at any location utilizing the chart review activity 142. Further, the patient call documentation activity 144 may be triggered, where clinical documentation 150 and/or customer service documentation 152 is entered. The system users may create customer service encounters in a call center environment using, for example, the customer service activity 174 where the encounters may be accessed via the messaging activity 178, or through relevant activities available to system users with the appropriate role-based security clearance. The entry of clinical documentation 150 may include entering a patient disposition 156, and scheduling information 162. Disposition 156 may include, but is not limited to, urgent care 158 and emergency department 160 dispositions. Entry of an urgent care disposition 158 may cause an urgent care window (not shown) to automatically open, where patient demographic information is pulled from the patient record of the enterprise database 24, and automatically displayed in relevant fields of the graphical user interface 22. System users may view arrival lists at urgent care facilities that have other products installed, and place patients on arrival lists from the patient call center environment. Where the emergency department disposition 160 is entered, an expected ER arrival window (not shown) may open, where users at the call center may enter relevant information for the patient, and place the patient on the ER arrival list at facilities where products (including Epic products) are installed directly from the call center.

Where scheduling information 162 is selected, an appointment may be scheduled via schedule appointment 164, or advanced scheduling may be jumped to as shown at box 166. System users may schedule an appointment at box 164 for the patient directly from the call center, where the appointment shows up on the provider's schedule as viewed from an Epic (or other companies) product provided within the health care information system that allows access to the patient and/or provider record. As shown at box 166, users with proper security may jump to an advanced scheduling activity, for example, included within appointment entry 172 to access more detailed scheduling tasks.

The patient demographics activity 146 maybe opened for entering/updating patient demographic information, and an order entry activity 154 may be opened, where call center system users are able to place orders that are administered at a different location, for example a flu shot. Once the order is filled, the patient record may be immediately updated to reflect the order, and health maintenance records for the patient are updated. Charges are dropped for the order, checked for correct coding, and matched to payor/plan information for the patient. Further, benefit and billing information may be handled by the relevant activities available to system users with billing security clearance using, for example, the account maintenance activity 176.

Users handling patient calls in a triage environment are able to access a patient's complete medical record, and enter information into the record in real time, so that users working at other locations and/or roles within the enterprise can view new patient information simultaneously. Specially customized forms may be used as an enterprise-added activity 148 to record call specifics. Providers can view and graph from these forms directly from the patient record as needed. Additionally, call center users can have more than one workspace open on their user interface at the same time for handling a single or multiple patients, allowing them to move between the workspaces with multiple calls quickly without losing the context and correct activity structure for each workspace (for example the workspace is rebuilt and displays correctly each time a user returns to it from another workspace). The "plug-in" design of the HCIS user interface allows each organization to determine which activities they want to use in their call center environments. For example, some organizations could choose to collect call information via customizable Smart-Forms, which would then appear as another tab on the activities toolbar 36, while others might use protocols that are included with the call center application.

Figure 6:
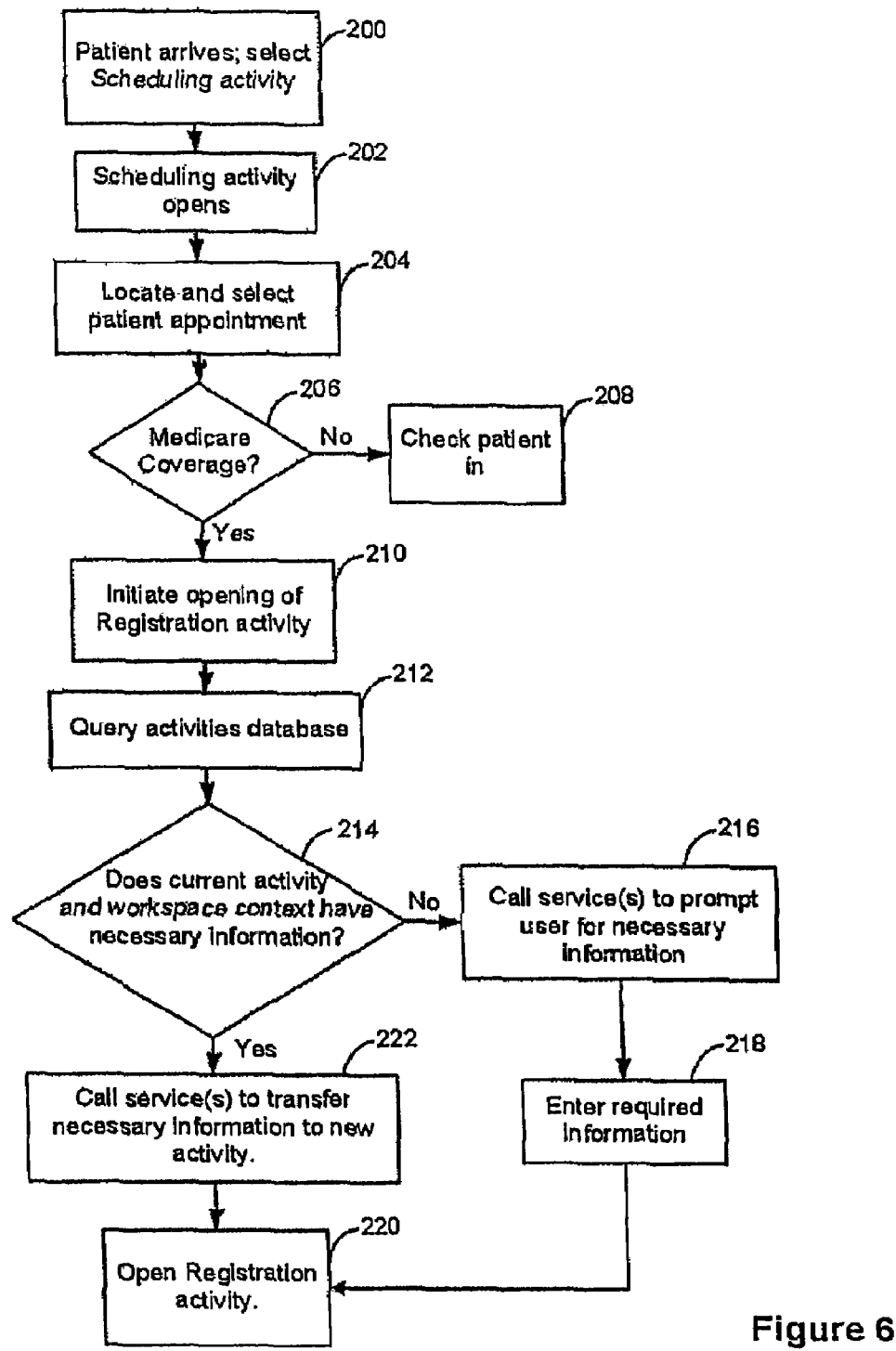
FIGS. 6 and 7 together illustrate functionality of the graphical user interface for providing Medicare Secondary Payor compliance in accordance with embodiments of the invention.
Figure 7:
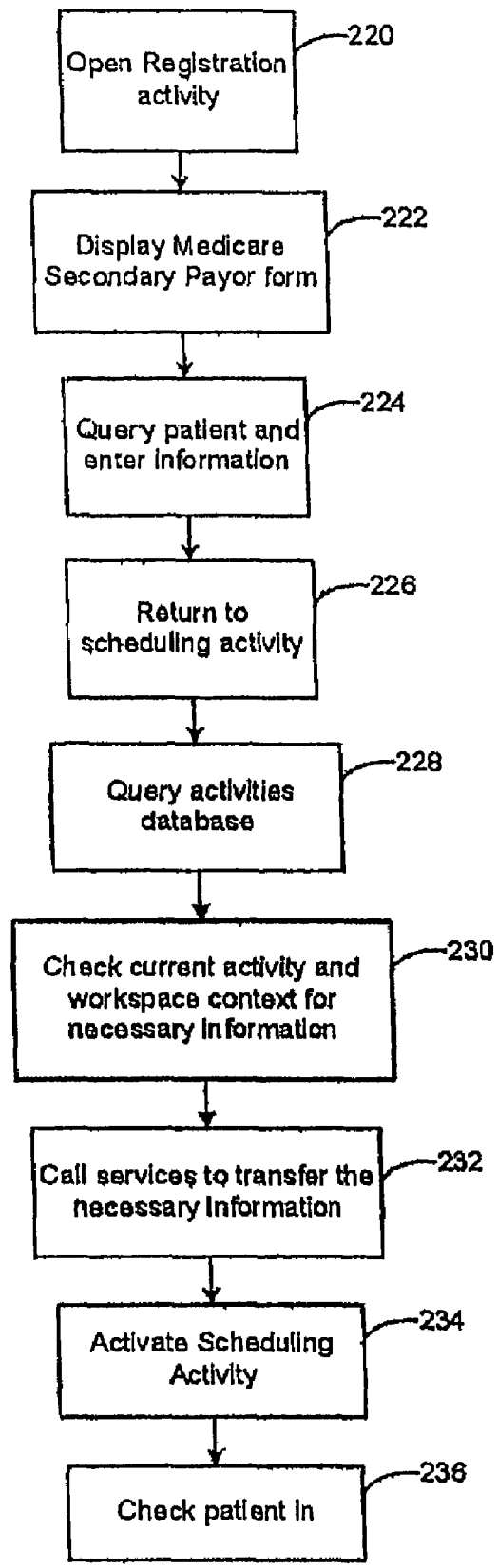

FIGS. 6 and 7 illustrate functionality of the HCIS graphical user interface for providing Medicare Secondary Payor (MSP) compliance in accordance with an embodiment of the invention. In this way, the invention can facilitate integrated workflows that help enterprises comply with MSP information regulations. These regulations require health care enterprises to collect certain information at each visit from patients who are covered by Medicare. A system user accesses the scheduling activity to check in any patient who has arrived for a scheduled appointment, step 200, which may include determining a patient's date of birth and/or age using the record for the patient. The system user may enter the scheduling activity by, for example, selecting the scheduling activity tab in the activity toolbar 36. The scheduling activity opens, step 202, and the system user locates and selects the patient's scheduled appointment, step 204. In step 206, the system checks whether there is Medicare coverage in the patient's visit account. Where there is no Medicare coverage in the patient's visit account, the user checks the patient in, as shown in step 208. However, where there is a Medicare coverage in the patient's visit account, the Medicare Secondary Payor information must be completed for the patient, and thus the system initiates the opening of the registration activity as shown in step 210. It is mandatory for clinical enterprises to collect Medicare Secondary Payor information for patients who participate in Medicare. The HCIS's flexible, plug-in framework makes it possible not only to automatically check the patient's account, but to automatically open the registration activity and require the system user to enter MSP information into a standard form.

Upon initiating the opening of the registration activity in step 210, the activities database 26 is queried to determine what data is necessary (the data requirements) to open the new activity, for example is a patient identification required to run the activity, as shown in step 212. The information provider 30 checks the current activity and workspace context for the necessary information, for example whether a patient is open in the current activity, step 214. Where the necessary data is not present in the current activity, the information provider 30 calls a service that prompts the user for the necessary information, step 216, and the user enters the required information as shown in step 218. The information provider's prompt to the system user may be, for example, a dialog box displayed in the workspace requesting the information from the system user. The system then opens the registration activity as shown in step 220. However, where the necessary information is present in the current activity in step 214, the information provider 30 calls services that transfer the necessary information to the new activity, as shown in step 222, and the workflow continues as shown in step 220 where the system opens a registration activity.

Referring to FIG. 7, where the system opens the registration activity, step 220, the registration activity displays the Medicare Secondary Payor form to the user, step 222. Under current regulations, the Medicare Secondary Payor information required by the government must be entered before the form can be closed. In step 224, the system user asks the patient the questions on the form and enters the information, and the system user returns to the scheduling activity to check in the patient, step 226. The system user may return to the scheduling activity, by for example, selecting the scheduling activity tab within the activity toolbar, or alternatively, by "clicking" a mouse connected to the graphical user interface in a portion of the workspace displaying the scheduling activity. In step 228, the activities database 26 is queried to determine the data requirements to open a new activity. The information provider 30 checks the current activity and workspace context for the data corresponding to the data requirements, and the information provider 30 calls services that transfer the necessary information to the new activity, step 232, where the current activity includes the necessary information. The workflow continues as shown in step 234 where the system activates the scheduling activity, and the system user checks the patient in, step 236. The configurability of this workflow allows the enterprise employing the invention guaranteed compliance with the MSP regulations in one workflow without interfacing information between applications, and without forcing the user to move back and forth between separate scheduling and registration applications or record information that must later be entered into a registration application by another user Although now shown, if the necessary information is not present within the current activity and work space context in box 230, services may be called to prompt the user for necessary information, where the user enters the necessary information similar to as discussed above with respect to boxes 216 and 218 of FIG. 6.

Figure 8:
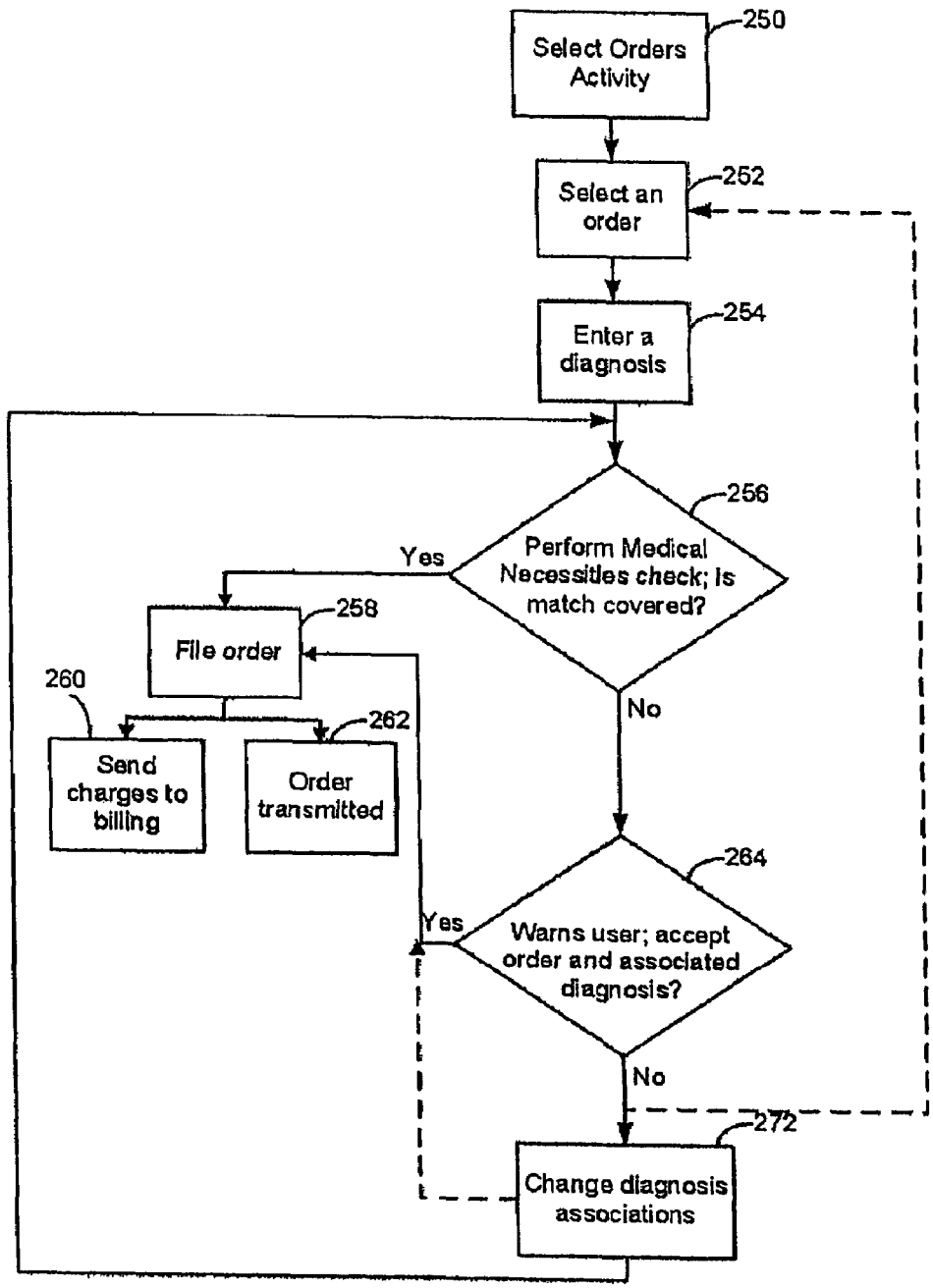
FIGS. 8 and 9 together illustrate functionality of the user interface for providing Health Care Financing Administrations Correct Coding Initiative by Local Medical Review Policy checking in accordance with embodiments of the invention.
Figure 9:
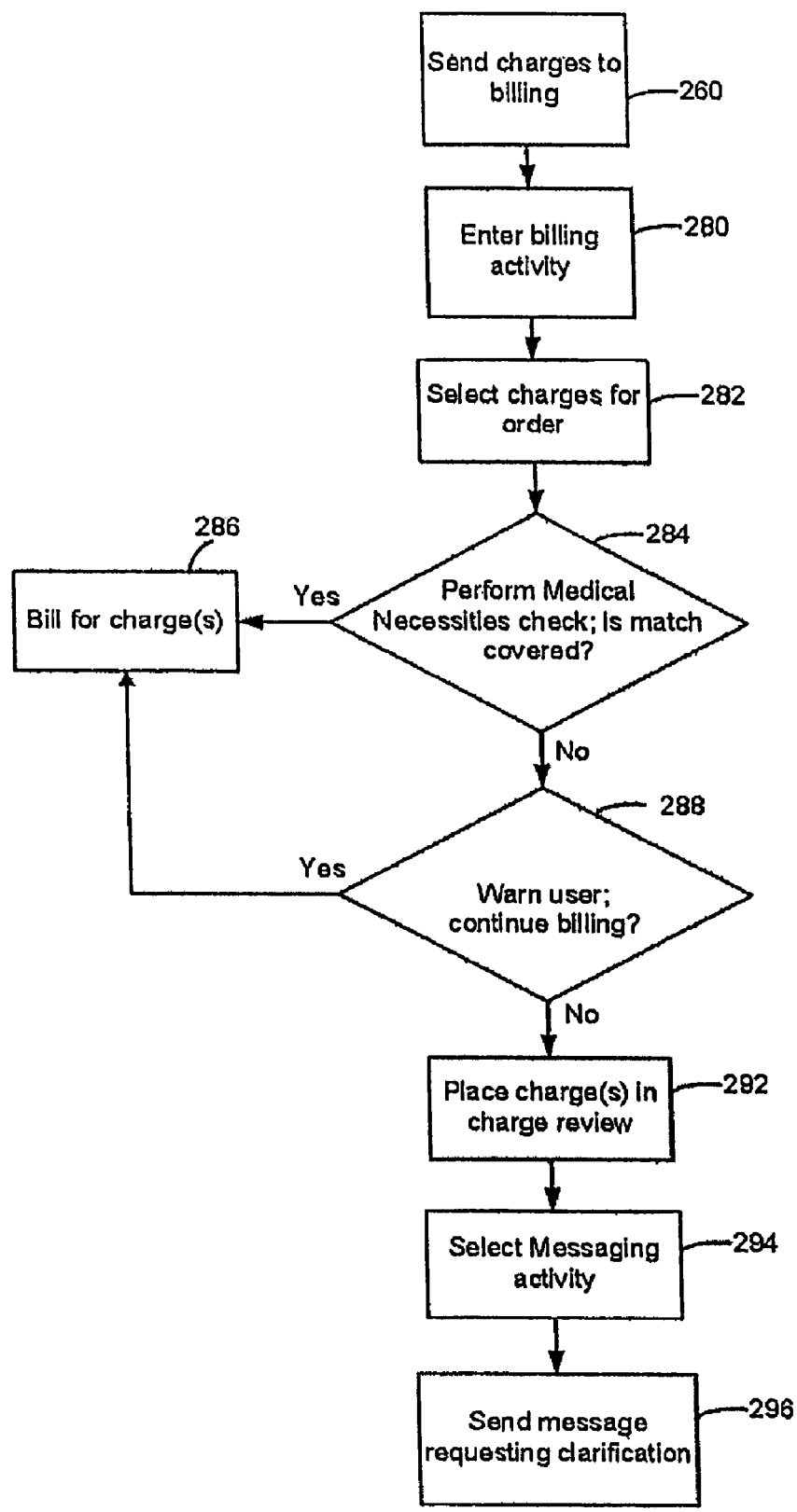

FIGS. 8 and 9 illustrate functionality of the user interface for providing Centers for Medicare and Medicaid Service (CMS) (formerly the Health Care Financing Administration correct coding initiative (CCI)) local medical review policy (LMRP) checking in accordance with an embodiment of the invention. These figures together show how the invention can facilitate integrated workflows that help enterprises comply with the CMS CCI by conducting LMRP checks in both the clinical and billing activities. The CCI encourages health care enterprises to use recognized order and diagnosis associations in order to ensure compliance with medical necessity requirements mandated by Medicare.

As shown in step 250, the system user working in the orders activity selects an order, step 252, and enters a diagnosis and associates it with the order, step 254. In step 256, the system performs a medical necessity check, drawing on preloaded LMRP information which compares the order and associated diagnosis to matches approved by LMRP edits. To comply with the CMS's CCI, the LMRP edit information can be checked from activities associated with orders and billing, helping clinicians to comply with medical necessity guidelines, and preventing clinicians from placing orders with diagnosis associations that might not be covered by insurance. It is determined whether the order and associated diagnosis match is covered. Where the match is covered, the system user files the order, step 258, the charges for the order are then sent to billing and the order undergoes order transmittal, step 260 and 262, respectively. However, where the match between the order and associated diagnosis is not covered, the system warns the system user that the associated diagnosis is not covered by LMRP and queries the user whether to accept the order and associated diagnosis, step 264. Where the order is accepted, flow returns to step 258 where the system user files the order, and charges for the order are sent to billing and the order undergoes order transmittal, steps 260 and 262, respectively. However, where the order is not accepted, the system user changes the diagnosis associations, step 272, and the workflow returns to step 256. Alternatively, the workflow returns to step 252 where the system user selects another order. As a further alternative, flow returns to step 258 where the system user files the order, and charges for the order are sent to billing, and the order undergoes order transmittal, steps 260 and 262, respectively.

As shown in FIG. 9, once the charges for the order are sent to billing, for example as specified by any of steps 260, 268 or 276, the system user enters the billing activity as shown in step 280. Similar to entering the scheduling activity as discussed above with respect to step 200 (FIG. 6), the system user may enter the billing activity by, for example selecting the billing activity tab of the activity toolbar. In step 282, the system user selects the charges for the order filed, for example, at box 258 of FIG. 8, and the system performs a medical necessity check, drawing on preloaded LMRP information, which compares the order and associated diagnosis to matches approved by LMRP edits, and it is determined whether the match is covered, step 284. To comply with CMS's CCI, the LMRP edit information may be checked from other activities, for example activities associated with orders and billing, facilitated by the flexible plug in framework 28. Where the match is covered in step 284, the system user bills for the charges as shown in step 286. However, where the match is not covered in step 284, the system warns the system user that the associated diagnosis is not covered by LMRP, and queries the system user whether to continue billing for the charges, step 288. As discussed above with respect to step 216 (FIG. 6), the query may be in the form of a dialog box displayed in the workspace requesting the information from the system user. Even if an order with a non-covered diagnosis association has been filed by the clinician, the billing user can be alerted to correct the billing for the order before it is sent. Where the system user indicates to continue billing for the charges in step 288, flow returns to step 286 where the system user bills for the charges. However, where the system user does not continue billing for the charges, the system user places charges in charge review, step 292, and the system user selects a workflow management tool provided, for example, as the electronic messaging activity, step 294. The system user sends the message to the user who filed the order, and the message asks for clarification of the reason for filing the non-covered diagnosis associations, step 296.

In an alternate embodiment not shown, where an Epic Care medical record review is utilized, the placing of changes in change review of box 292 is done automatically by the HCIS, and thus need not be done by the system user.

The ability to conduct LMRP checks from multiple activities, which can alert various users to the same irregularities, is just one example of the integrated way in which an enterprise may use the invention to achieve a high rate of compliance with regulations that simultaneously affect disparate aspects of the health care enterprise.

The workflow management tool discussed above is provided as an Electronic Messaging and Workflow System. The Electronic Messaging and Workflow System (i.e. In Basket) enhanced by this invention is a comprehensive integrated interface that provides information, makes users aware of alerts and tasks that require their attention, and accesses relevant features of their applications.

In Basket is a feature which may be shared by Epic applications, and typically appears in various forms in all interfaces, including the EpicDesktop. While its basic function is to communicate messages to recipients, there is a great deal of specialization in terms of how messages are generated, and what users can do when they receive them. A plurality of specialized message types available, with some providing general features, for example, entering phone messages into In Basket resembling the common 'While you were out . . . ' forms, and others being specialized in nature, for example, allowing the revision of orders for lab tests after the order has been sent to the lab.

As an Electronic Messaging System, In Basket may collect messages sent to a system user and display them. Many messages require little or no action and are, in essence, reports. Common messages of this type include, for example, staff messages, phone calls, test results, and the 'covered work' message from the patent.

As a Workflow System, In Basket may make available a cross-section of features from Epic's applications provided by the health care system. Many 'messages' contain a link to some area of an application, or present their own interface for the recipient to take action. A common message of this type may provide a link to an encounter and ask the recipient to cosign an order for a medication. In this example, the message appears in an In Basket interface on the graphical user interface, and opening the message also opens a patient's medical record associated with the order. In another example, a similar message opens an incomplete telephone encounter so that the system user can address the issues raised by the phone call. Messages can be sent, for example, to a system user personally, to a group to which a system user belongs, to the workstation at which a system user is working, to any system user who has a particular patient's record open, and may be sent using other methods of identifying recipients. Many applications provided by the healthcare system have features to generate electronic messages. When results (i.e. blood sugar, blood pressure, etc.) are entered (or received from a lab) for a patient, messages may be automatically generated to report those results to the provider who ordered the test. Such messages may be generated based on an urgency level of the test results. For example, messages may be generated any time test results are obtained for the patient, generated when the test results fall within a predetermined range defined as 'abnormal', or generated when the test results fall within a predetermined range defined as a 'panic' range, where the system user is able to configure the urgency level at which the message(s) will be sent.

Further, paging capabilities may be incorporated in, or linked with, the system to allow system users to be paged when a message is received for that system user.

The electronic messages are typically completed when the action required by the message is taken. For example, for report-type messages, a system user receiving the message merely needs to read the message and mark the message as 'done.' For other messages, a system user may need to take some specific action, such as cosign an order or schedule an appointment before the electronic message is complete. When the information displayed is refreshed, completed messages are no longer displayed.

The functionality provided by the messaging and workflow system may be preferably embedded within the health care system, or operate as stand-alone functionality in conjunction with the health care system. Further, the messaging and workflow functionality is typically supported by the various parts of the HCIS data repository 20, as would be appreciated by one skilled in the art. For example, the enterprise database 24 may maintain various files of information (i.e. threshold values defining urgency level of test results, defining message distribution lists, etc.). The activities database 26 may include program structure to provide the messaging functionality along with the other various activities offered by the health care system, including (but not limited to) performing checks on information entered (or received) into a particular patient record which may necessitate automatic generation of a message to a system user. Many messages provide system users with the option of accessing one or more activities. The options are defined in terms of the activity which is made available, in that the option (typically a button or menu selection) is based on a Menu record recording the activity launched when the button is clicked or the menu option is selected. The info provider 30 may operate in conjunction with the activities database 26 in providing the messaging functionality with any required information. If the activity provides patient-specific information, the info provider, having identified a patient as the topic of the message, passes that patient to the activity. This allows the activity to open without first prompting the user for a patient. The plug-in HCIS framework 28 may allow the messaging and workflow functionality to be displayed or otherwise presented to a system user within the HCIS graphical user interface 22.

The invention has been described in terms of several embodiments, including a number of features and functions. Not all features and functions are required for every embodiment of the invention, and in this manner the invention provides a flexible system by which the plug-in framework allows additional activities to be added to the system without the difficulties associated with interfacing and configuring the activities to work with the HCIS and with each another. Further, the ease of interfacing applications due to the plug-in framework results in a high rate of compliance with government regulations. The common menu structures and common visual components provided by the graphical user interface provide system users with an intuitive interface with the HCIS, reducing the training requirements of system users. Further, the graphical user interface and plug-in framework allows system users to seamlessly switch between activities available within the HCIS, not requiring exiting of one program and entry into another program. Additionally, a single data repository used by the activities virtually eliminates data duplication between activities, and eliminates the difficulties associated with interfacing multiple databases having varying structure or format. In addition, the single data repository allows a common security record to be kept for system users, facilitating uniformity of security access for system users across all activities of the HCIS, ease of setting security requirements for new system users, and reduced probability of granting mistaken security privileges as security information for all activities need be entered but once. Further, the single data repository and plug-in framework allows an alert system to be provided to alert system users where information entered in an activity conflicts with other information for a particular patient in the data repository. In addition, system users are provided the ability to user-define the graphical user interface giving the flexibility of tailoring the graphical user interface to offer functionality and information to better serve the user's specific needs.

Although the single data repository has been described as a server in the preferred embodiment, one skilled in the art would realize that any application specific programming language, hardware, processor(s), and memory may be combined to perform the functionality of the components for the single data repository. Additionally, the enterprise database and the activities database may reside on the same storage device, or separate storage devices in communication with the information provider and the plug in framework while still being accessible and usable for all activities, where the communication link may be the internet, a data bus, or any other means for communicating information, as would be understood by one skilled in the art. Further, although the enterprise database 24 has been disclosed in various embodiments as including data collected for each patient in a single record, one skilled in the art would realize that advantages may be achieved from at least the common menu format and visual components provided by the graphical user interface as discussed herein where information for patients and/or security information is stored in more than one record per patient. In addition, the graphical user interface may be displayed on any display device, including a cathode ray tube device, Liquid Crystal Display, or any other device capable of conveying information to a system user, where the display device may be associated with a personal computer, server, handheld electronic device, etc.

The features discussed herein are intended to be illustrative of the features that may be implemented, however, such features should not be considered exhaustive of all possible features that may be implemented in a system configured in accordance with the preferred embodiments of the invention.

What we claim is:

1. An electronic healthcare system, comprising:
   a graphical user-interface;
   at least one electronic computer communicating with the graphical user interface to provide:
   (a) at least one electronic healthcare database including medical records;
   (b) a set of different software applications usable in any order by a single user on the electronic computer, the different software applications allowing a user to access different records of the electronic healthcare database for each of different patients;
   (c) a provider program running on the at least one electronic computer to:

(i) receive input from a user through the graphical user-interface identifying multiple software applications to be initialized and opened for at least two different patients;
(ii) provide multiple graphical workspaces each defining an area holding initialized and opened software applications, each graphical workspace visually linking only the multiple software applications accessing records of a single patient of the at least two different patients;
(iii) require first user actions to switch among software applications within a workspace and second user actions distinct from the first user actions to switch among workspaces of the at least two different patients; and
(iv) require a user to switch between workspaces before and in order to switch between a first and second initialized and opened software application accessing different patients; whereby confusion between records of different patients is reduced;
wherein the provider program further provides multiple different graphical indications each associated with applications accessing different common patients, the different graphical indications visually distinguishing among the multiple software applications accessing records of different patients.

2. The electronic healthcare system of claim 1 wherein the provider program further accepts input from a user to switch between workspaces.

3. The electronic system of claim 2 wherein the user input is from a mouse, a predetermined key, or a stylus.

4. The electronic healthcare system of claim 1 wherein the provider program further accepts input from a user to switch between software applications within a workspace.

5. The electronic system of claim 4 wherein the user input is from a mouse, a predetermined key, or a stylus.

6. The electronic system of claim 1 wherein each workspace allows only a different subset of software applications to be opened and initialized.

7. The electronic system of claim 6 wherein the software applications are collected from software applications selected from the group consisting of: order entry, charts and graphs, chart review, results review, registration, flowsheets, patient alerts, snapshot, visit navigator, patient history, patient demographics, and an enterprise added activity.

8. The electronic system of claim 1 wherein data entered through a first software applications may cause an automatic opening and initialization of a second software application accessing records of a same patient as accessed by the first software application.

* * * * *